United States Patent
Gore et al.

(10) Patent No.: US 6,789,421 B2
(45) Date of Patent: Sep. 14, 2004

(54) DENSITY-BASED FUEL INDICATOR SYSTEM FOR FUEL CELLS

(75) Inventors: Makarand P. Gore, Corvallis, OR (US); L. Chris Mann, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 79 days.

(21) Appl. No.: 10/044,088

(22) Filed: Jan. 11, 2002

(65) Prior Publication Data

US 2003/0131663 A1 Jul. 17, 2003

(51) Int. Cl.[7] .............................. G01N 9/00; H01M 2/38
(52) U.S. Cl. ............................................ 73/444; 429/34
(58) Field of Search ..................... 73/444, 445, 446, 73/447, 448, 451, 452, 453, 454, 32 R; 429/34, 14, 25, 38, 39, 53, 54, 55, 56, 57, 91

(56) References Cited

U.S. PATENT DOCUMENTS

| | | | | |
|---|---|---|---|---|
| 3,808,893 A | * | 5/1974 | Jinno et al. ..................... 73/452 |
| 3,952,761 A | * | 4/1976 | Friedland ..................... 73/452 |
| 4,061,839 A | * | 12/1977 | Kubler ........................ 73/453 |
| 4,353,253 A | * | 10/1982 | Callahan ..................... 73/454 |
| 4,400,978 A | * | 8/1983 | Guay et al. ................... 73/453 |
| 4,442,700 A | * | 4/1984 | Swoboda ..................... 73/32 A |
| 4,443,424 A | * | 4/1984 | Olson ....................... 423/576.6 |
| 4,496,637 A | * | 1/1985 | Shimada et al. .............. 429/44 |
| 4,650,729 A | * | 3/1987 | Nakamura et al. ............ 429/61 |
| 4,700,580 A | * | 10/1987 | Kamin ..................... 73/864.51 |
| 4,967,595 A | * | 11/1990 | Olson ......................... 73/440 |
| 5,518,831 A | * | 5/1996 | Tou et al. ..................... 429/42 |
| 5,534,363 A | * | 7/1996 | Sprouse et al. ............... 429/34 |
| 5,824,885 A | * | 10/1998 | Lekholm ..................... 73/444 |
| 6,408,694 B1 | * | 6/2002 | Lin et al. ..................... 73/444 |
| 6,506,513 B1 | * | 1/2003 | Yonetsu et al. ............... 429/34 |

FOREIGN PATENT DOCUMENTS

JP          2-37881     *  2/1987

* cited by examiner

*Primary Examiner*—Helen C. Kwok (57) ABSTRACT

A means for determining the concentration of a hydrogen-rich fuel in a fuel solution within the anode reservoir of a fuel cell. The fuel concentration is determined using a float responsive to fuel solution density. As fuel is consumed, the fuel concentration decreases. As the fuel concentration decreases, the density of the fuel solution increases, causing the float to rise. A window may be included in the anode reservoir or in an attached float chamber to facilitate inspection of the position of the float. A fuel scale may be included to facilitate fuel concentration determination based on the position of the float within the fuel solution. Additionally, a valve responsive to float position may act to control fuel delivery.

15 Claims, 7 Drawing Sheets

DENSITY-BASED FUEL INDICATOR SYSTEM FOR FUEL CELLS

TECHNICAL FIELD

The present invention relates to fuel cells, and, in particular, to a density-based fuel indicator system for use with fuel cells.

BACKGROUND OF THE INVENTION

Fuel cells produce electrical energy by reacting a fuel with an oxidant, usually in the presence of a catalyst. Typically, fuel cells consist of a fuel electrode, or anode, and a reducing electrode, or cathode, separated by an ion-conducting electrolyte. An external conductor connects the electrodes to an electrical circuit, or load. In the conductor, current is transported by the flow of electrons. In the electrolyte, current is transported by the flow of ions.

Figure 1:
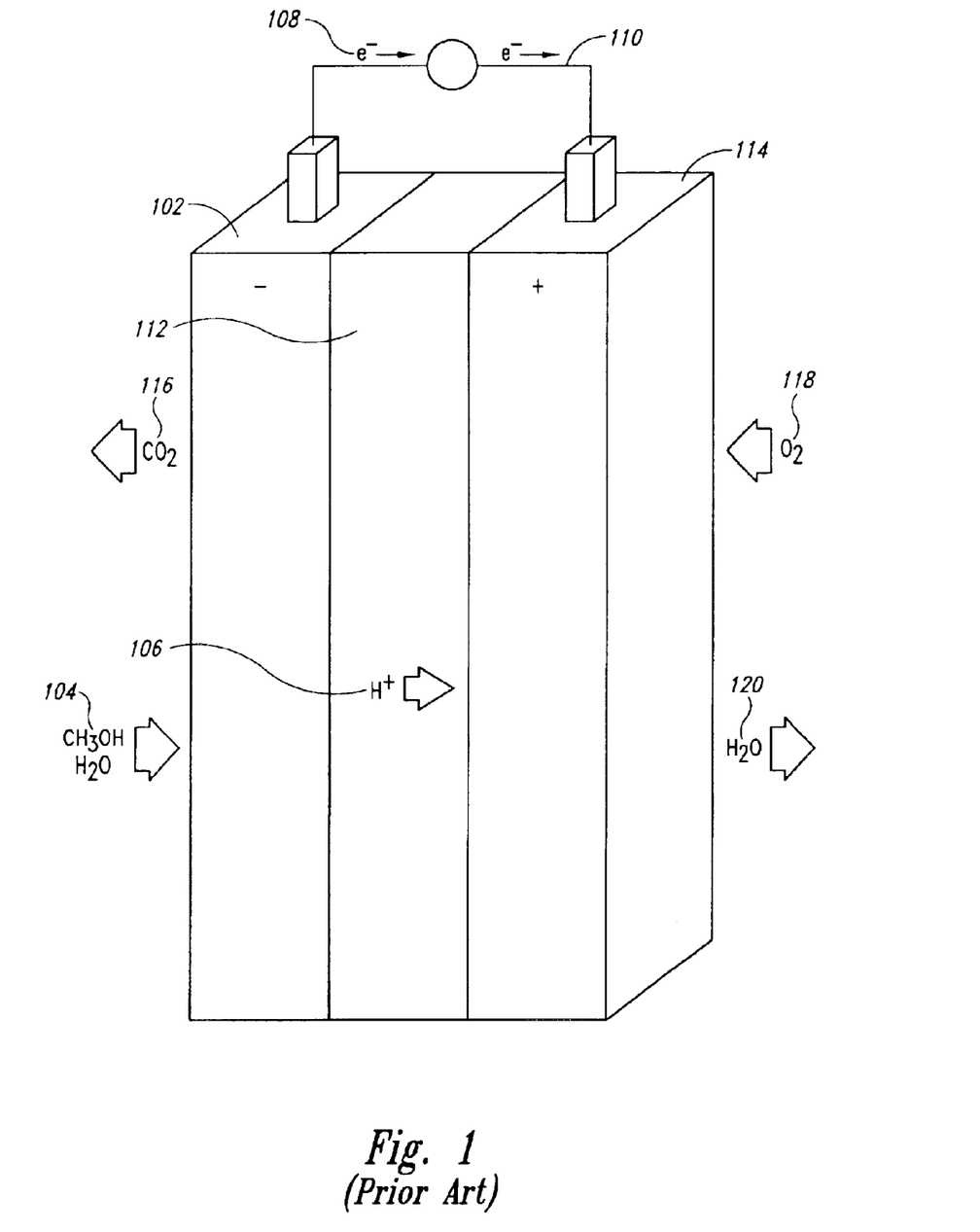
FIG. 1 is a diagram of a methanol fuel cell.

Any number of hydrogen rich fuels may be used as a fuel source, such as methanol, ethanol, butane, and propane. FIG. 1 is a diagram of a methanol fuel cell. A reservoir that includes the anode, or anode reservoir 102, contains a methanol-water solution 104. The methanol fuel cell generally is in a charged state when the percentage of methanol in the methanol-water solution is relatively large. As methanol is oxidized and electricity is generated by the fuel cell, the percentage of methanol in the methanol-water solution decreases and the fuel cell becomes depleted.

The methanol contained within the methanol-water solution is oxidized, usually in the presence of a catalyst, producing hydrogen ions 106, electrons 108, and carbon dioxide 116. This oxidation reaction occurs inside the anode reservoir 102 of the fuel cell. A primary anode oxidation reaction is shown below:

$$CH_3OH + H_2O \rightarrow CO_2 + 6H^+ + 6e^-$$

Note that, since the electrolyte is a relatively poor electrical conductor, electrons 108 flow away from the anode via an external circuit 110. Simultaneously, hydrogen ions 106 travel through the electrolyte, or membrane 112, to the cathode 114. Commonly used membranes include Nafion 112®, Nafion 117®, and polybenzimidazole.

At the cathode 114 of a fuel cell, oxygen 118 is reduced by hydrogen ions 106 migrating through the electrolyte 112 and incoming electrons 108 from the external circuit 110 to produce water 120. The primary cathode reaction is shown below:

$$3/2 O_2 + 6H^+ + 6e^- \rightarrow 3H_2O$$

The individual electrode reactions, described above as primary anode and primary cathode reactions, result in an overall methanol-fuel-cell reaction shown below:

$$2CH_3OH + 3O_2 \rightarrow 2CO_2 + 4H_2O + electricity$$

Additional minor chemical reactions may occur, and thermal energy is generally produced.

Modern fuel cells can continuously produce electrical current for long periods of time without the need for recharging. However, fuel cells produce electrical charge only when fuel is present in the anode reservoir above a threshold concentration. Therefore, in order to ensure continuous operation of a fuel cell, an indication of the amount of fuel remaining in the fuel cell needs to be easily obtainable. Fuel cells commonly provide no convenient, cost-efficient means for reliably determining the amount of available fuel remaining in the fuel cell. Therefore, designers, manufacturers, and users of fuel cells have recognized the need for a convenient, cost-efficient means for determining the amount of fuel remaining in a fuel cell.

SUMMARY OF THE INVENTION

One embodiment of the present invention provides a means for determining the concentration of methanol within an anode reservoir of a methanol-based fuel cell. The methanol concentration is determined through the use of a float that responds to the density of the methanol-water solution. As methanol is consumed during normal operation of the fuel cell, the methanol concentration of the methanol-water solution decreases and the density of the methanol-water solution correspondingly increases. The float is fabricated to have a density such that, as methanol is consumed, the float rises from a lower position within the anode reservoir, or within a float chamber in fluid communication with the anode reservoir, to a higher position in the anode reservoir or float chamber. A fuel scale may be included with the fuel cell to facilitate determination of the methanol concentration by visual comparison of the float position with markings on the fuel scale corresponding to fuel concentrations. Additionally, a valve responsive to the position of the float may act to control fuel delivery. Alternative embodiments may employ different types of hydrogen-rich fuels.

DETAILED DESCRIPTION OF THE PREFERRED EMBODIMENT

The present invention provides a means to determine the concentration of fuel within a fuel cell. In one embodiment, a float is suspended in a methanol-water solution contained in the anode reservoir, or a float chamber in fluid communication with the anode reservoir, and is visible through a transparent window. Normal operation of the fuel cell lowers the concentration of methanol in the methanol-water solution within the anode reservoir. As the concentration of methanol decreases, the density of the methanol-water solution increases. The float, having a density intermediate between the density of water and methanol, continuously rises from a lower position to a higher position as methanol is consumed and the density of the methanol-water solution increases. Thus, the position of the float corresponds to the concentration of methanol in the methanol-water solution. A fuel scale may be included to facilitate methanol concentration determination based on the float position in the methanol-water solution.

Figure 2A:
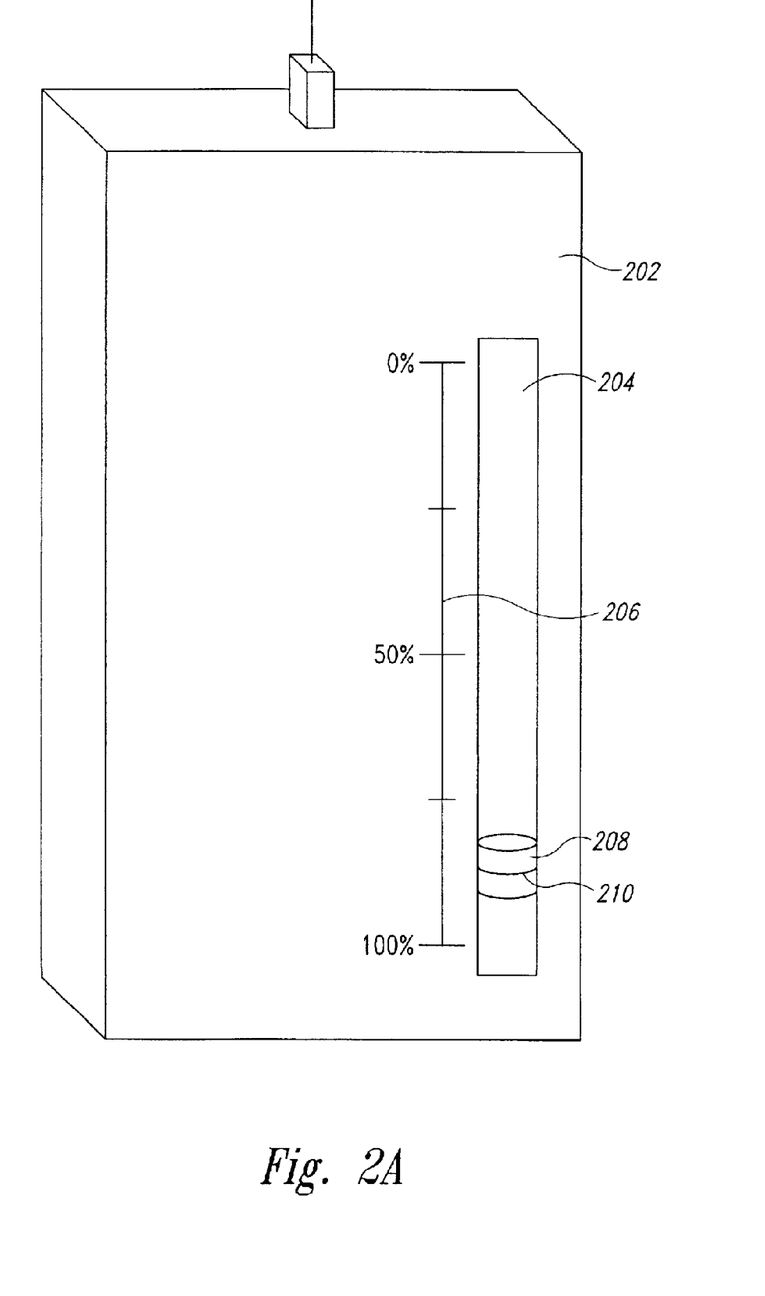
FIG. 2A shows a density-based fuel indicator in direct contact with the anode reservoir.

FIG. 2A illustrates one embodiment of the present invention with a density-based fuel indicator in direct contact with the anode reservoir. The anode reservoir 202 includes a long, thin vertical window 204 visible from the exterior of the fuel cell. A fuel scale 206, affixed to the exterior of the fuel cell, extends along the vertical length of the window 204. The fuel scale 206 is shown as a vertical line with a series of evenly spaced marks, each mark representing a fuel concentration.

FIG. 2A shows a float 208, suspended in fluid of a particular density, visible through a window 204 in the anode reservoir 202. The float 208 utilizes a horizontal fuel indicator bar 210 to facilitate fuel concentration determination. The position of the fuel indicator bar 210 corresponds to a percentage of available fuel remaining. In FIG. 2A, the position of the float 208 corresponds to a methanol concentration at which 87% of the available fuel supply remains.

Figure 2B:
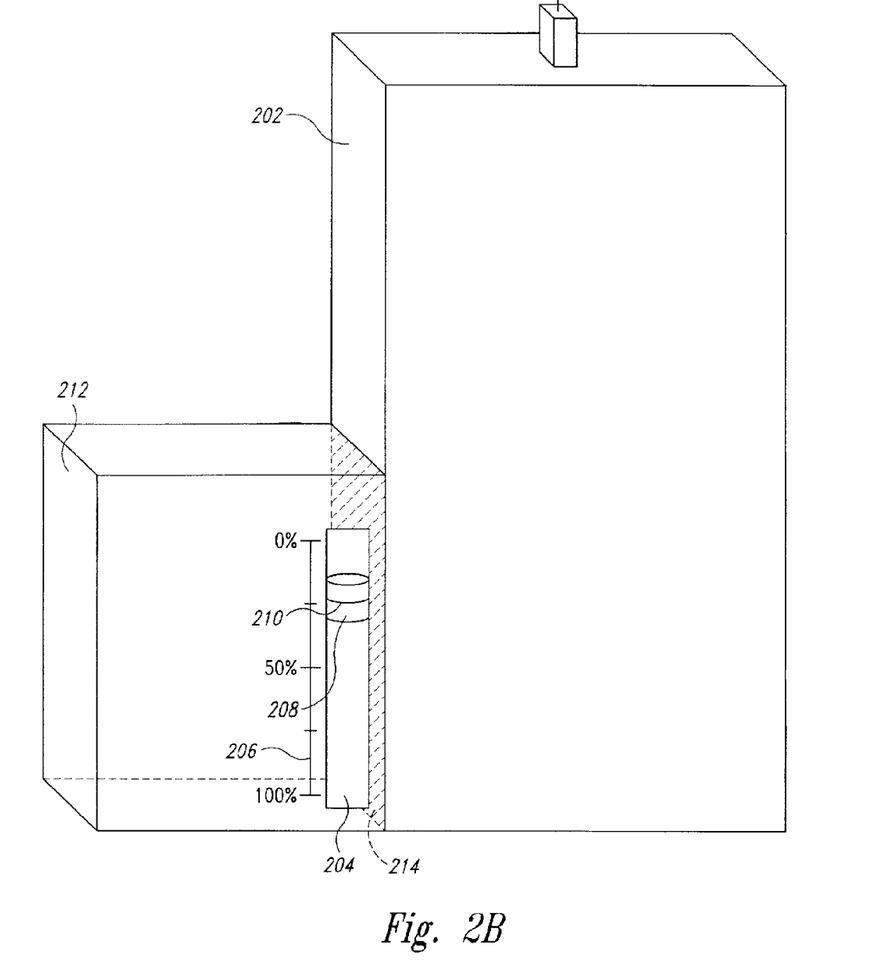
FIG. 2B shows a float chamber with a density-based fuel indicator separated from the anode reservoir by a membrane.
Figure 2C:
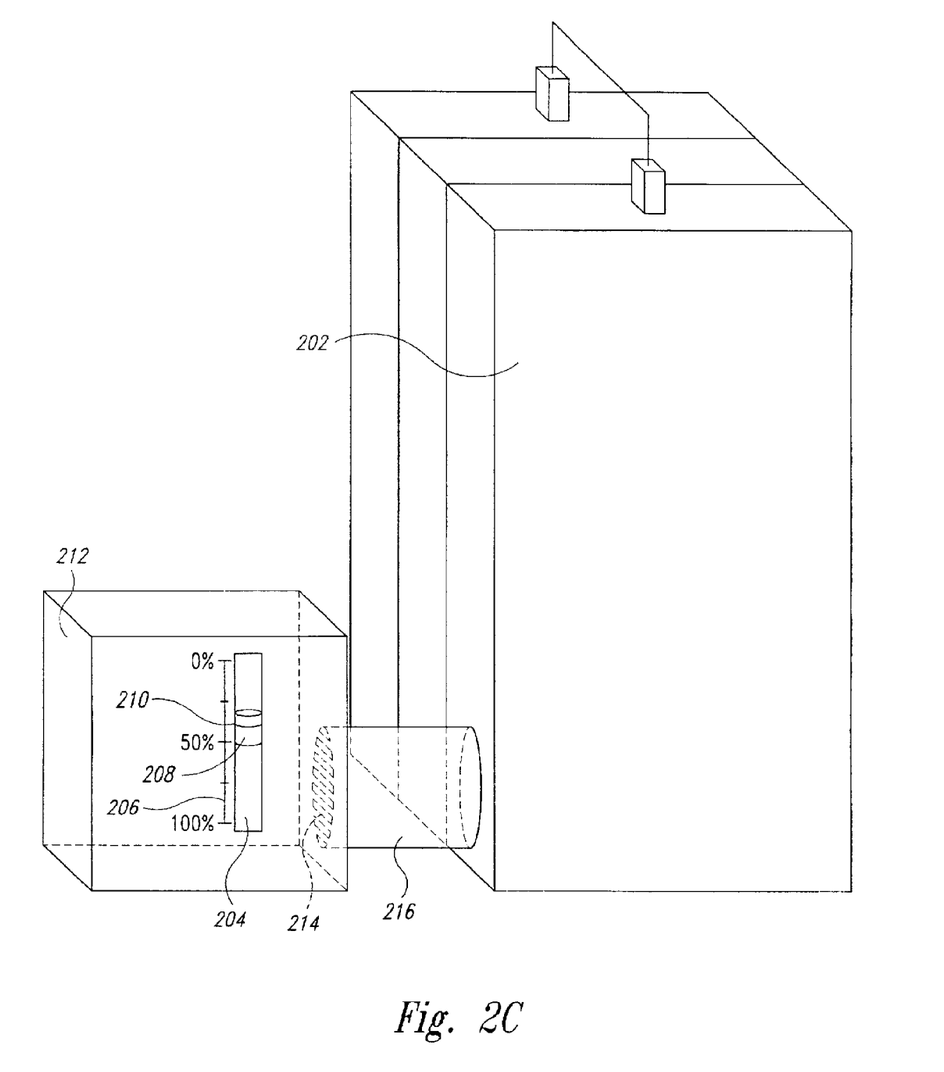
FIG. 2C shows a float chamber with a density-based fuel indicator separated from the anode reservoir by a fuel channel and an optional membrane.

In the above-described embodiment, shown in FIG. 2A, the float is contained directly inside the anode reservoir. In alterative embodiments, a float chamber in fluid contact with the anode reservoir may contain the float. FIG. 2B shows a float chamber 212 separated from the anode reservoir 202 by a semi-permeable membrane 214. In FIG. 2B, the float 208 position corresponds to a methanol concentration at which 25% of the available fuel supply remains. In FIG. 2C, a float chamber is separated from the anode reservoir by a fuel channel. The fuel channel 216 may have variable lengths and shapes, but must have a cross sectional area large enough to allow for equilibration of the methanol concentration in the float chamber 212 within a reasonable time frame. Note that the position of the float 208 corresponds to a methanol concentration at which 40% of the available fuel supply remains.

Suspension of the float 208 within the methanol-water solution requires the float 208 to have a density intermediate to the density of pure methanol and the density of pure water. The float 208 is often attached to a long cylinder, whose depth within the methanol-water solution depends on the density of the methanol-water solution. The movement of the float 208 within the methanol-water solution follows Archimedes' principle, according to which the buoyant force on a body immersed in a fluid is equal to the weight of the fluid displaced by that object. Therefore, provided the weight and volume of a float immersed in a fluid remains constant, the float rises as the fluid surrounding the float becomes more dense.

Figure 3A:
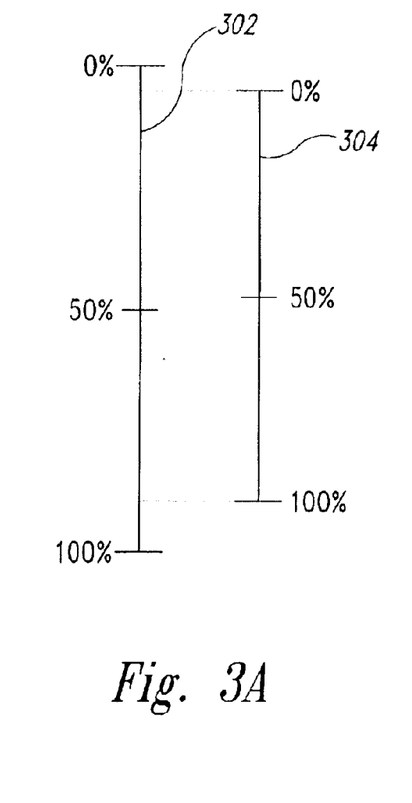
FIG. 3A shows the relationship between an absolute fuel scale and an available-fuel-remaining fuel scale.
Figure 3B:
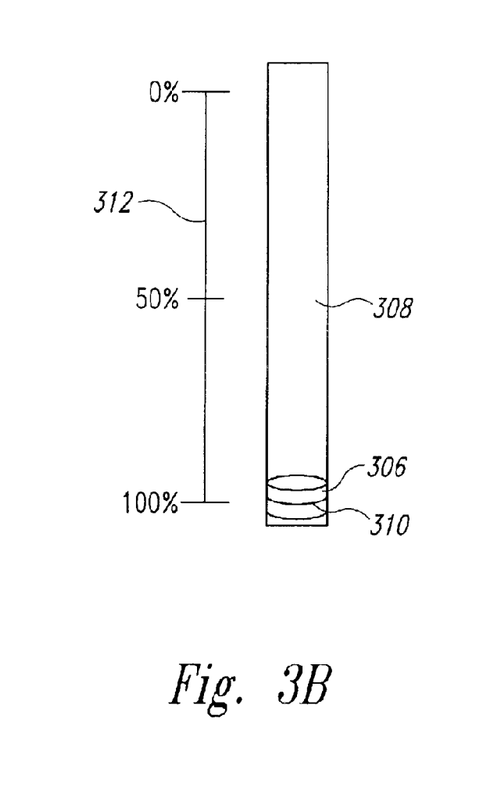
FIGS. 3B–C show the effect of fluid density on float position.

The fuel indicator system of the present invention determines the methanol concentration in a methanol-water solution by using the differences in densities between methanol-water solutions having high methanol concentrations and methanol-water solutions having low methanol concentrations. FIGS. 3A–B show the effect of fluid density on float position. The density of pure water is 1.0000 kg/m$^3$, and the density of pure methanol is 0.7931 kg/m$^3$ at 20° C. and atmospheric pressure of 1.00 atm. As methanol is consumed during operation of the fuel cell, the density of the methanol-water solution increases in relation to the decreasing concentration of methanol in the solution and the corresponding increase in concentration of water in the solution. For instance, at 0.5% methanol in water, the density is 0.9991 kg/m$^3$ at 20° C.

FIG. 3A shows two different types of fuel scales. The fuel scale on the left 302 is an absolute scale that shows methanol concentrations in a methanol-water solution ranging from pure methanol to pure water. The fuel scale on the right 304 is a scale showing the available fuel remaining. The fuel scale on the right 304 is shorter than the fuel scale on the left 302 because the fuel scale on the right 304 encompasses a smaller range of fuel concentrations. Methanol fuel cells operate using methanol in a methanol-water solution. Consequently, a fully-charged fuel cell of this embodiment contains a methanol-water fuel solution having a methanol concentration less that 100%, and a depleted fuel cell of this embodiment may contain a methanol-water solution having a methanol concentration greater than 0%.

Figure 3C:
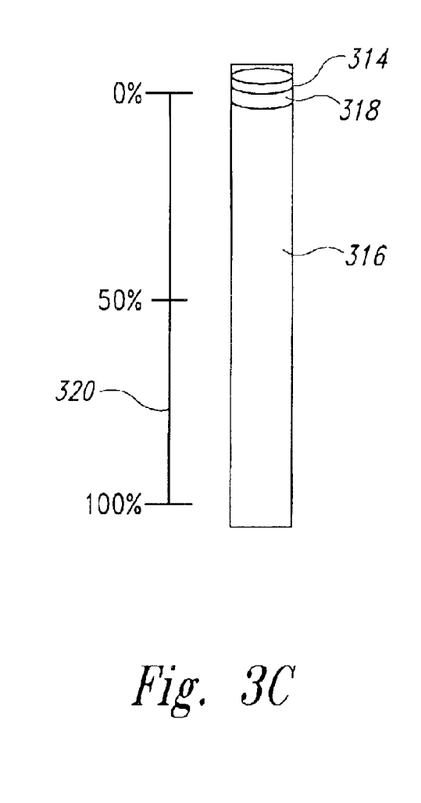

FIG. 3B shows a float in a charged methanol-water solution. The methanol-water solution has a high methanol concentration and a relatively low density. In a solution of relatively low density, the float 306 sinks to the lower edge of the window 308 and the fuel indicator bar 310 corresponds to a value of 100% on the fuel scale 312. FIG. 3C shows a float in a depleted methanol-water solution. The methanol-water solution has a low methanol concentration and a relatively high density. In a solution of relatively high density, the float 314 rises to the upper edge of the window 316 and the fuel indicator bar 318 corresponds to a value of 0% on the fuel scale 320.

Figure 4A:
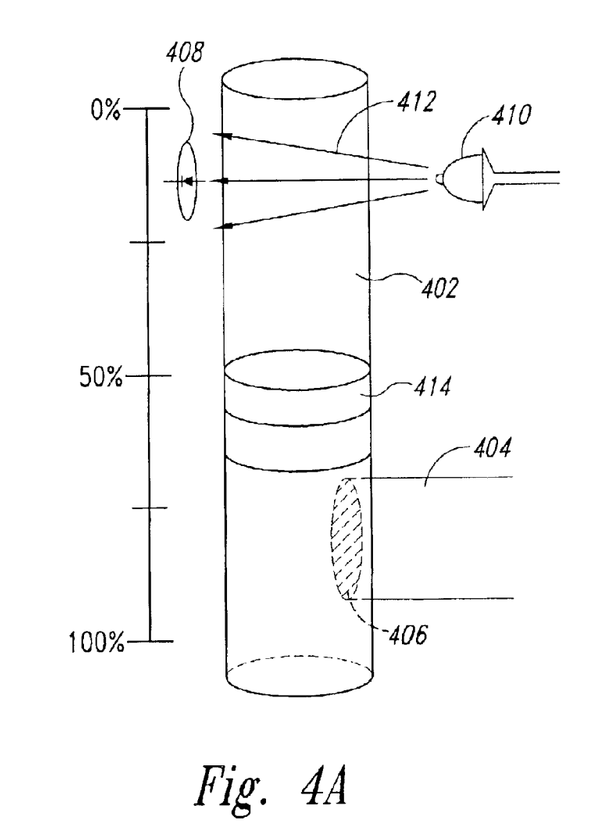
FIGS. 4A–B illustrate an embodiment of the present invention with the fuel delivery controlled by the float.
Figure 4B:
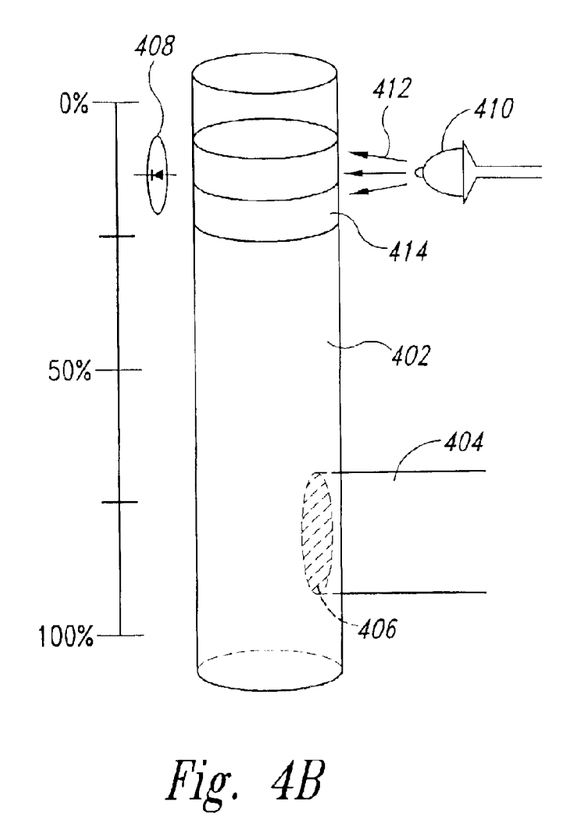
Figure 5:
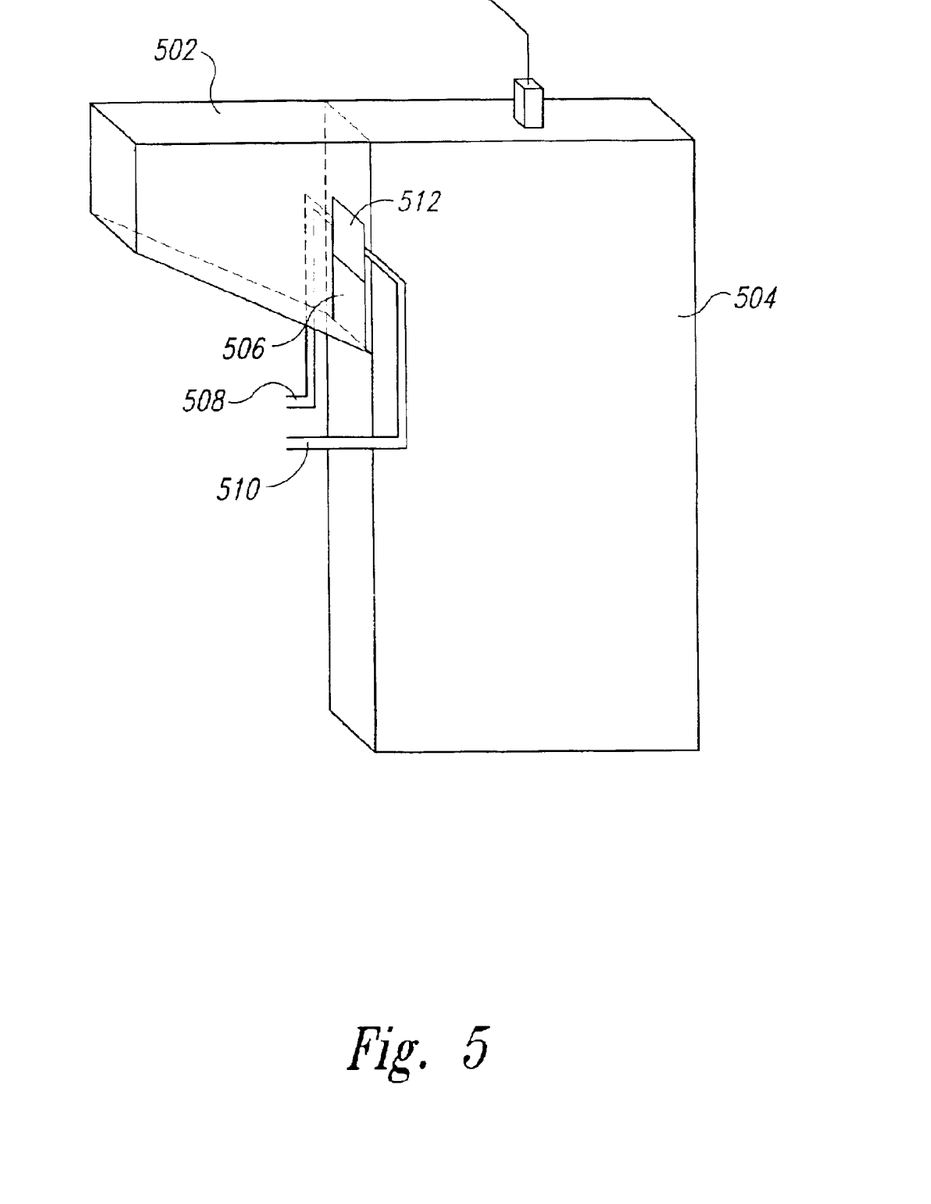
FIG. 5 illustrates one embodiment of a fuel delivery mechanism.

FIGS. 4A–B and 5 illustrate an embodiment of the present invention with the float controlling the release of methanol into the anode reservoir. FIGS. 4A–B show a float chamber 402, incorporating a density-based fuel indicator system, separated from the anode reservoir by a fuel channel 404 and a semi-permeable filter membrane 406. The float chamber 402 contains a photodiode 408 and a light emitting diode ("LED") 410. The LED 410 shines light 412 upon the photodiode 408 through the methanol-water solution in the float chamber 402. FIG. 4A shows the float 414 in the lower portion of the float chamber 402, indicating a relatively high concentration of methanol. The light 412 from the LED 410 reaches the photodiode 408 and the photodiode 408 remains deactivated. The float 414 rises within the methanol-water solution as methanol is consumed during operation of the fuel cell. FIG. 4B shows the float 414 in the upper portion of the float chamber 402, indicating a relatively low concentration of the methanol. At a predetermined methanol level, the float rises high enough to block light 412, produced by the LED 410, from reaching the photodiode 408, thus activating the photodiode 408. The photodiode 408 produces an electric current that triggers a mechanism to release fuel into the anode reservoir.

Alternately, at a predetermined methanol level, the light 412 produced by the LED 410 activates the photodiode 408. As the float 414 rises during operation of the fuel cell, the float 414 ceases to block light 412, produced by the LED 410, from reaching the photodiode 408, thus activating the photodiode 408. Consequently, the photodiode 408 produces an electric current that triggers a mechanism to release fuel into the anode reservoir. Note that FIG. 4 omits the window for clarity of illustration. Note also that FIG. 4 shows the float chamber 402 as a different shape than in previous illustrations, for clarity of illustration. Alternative embodiments employ the photodiode 408 and LED 410 within the anode reservoir.

One embodiment of the fuel release mechanism, shown in FIG. 5, comprises a fuel reservoir 502 separated from the anode reservoir 504 by a door 506. The fuel reservoir contains nearly pure methanol without excess water added. Two wires 508,510, extending from the photodiode, 408 in FIG. 4, are in contact with a valve 512 that controls the aperture of the door 506. At a predetermined methanol level, the float rises enough to block the light from reaching the photodiode, thus activating the photodiode. An electric circuit is completed that signals the valve 512 to open the door 506. Gravity allows the methanol in the fuel reservoir 502 to be released into the anode reservoir 504. Alternatively, at a predetermined methanol level, the float rises enough to cease blocking the light from reaching the photodiode, thus activating the photodiode. An electric circuit is completed that signals the valve 512 to open the door 506. Gravity allows the methanol in the fuel reservoir 502 to be released into the anode reservoir 504.

Although the present invention has been described in terms of a particular embodiment, it is not intended that the invention be limited to this embodiment. Modifications within the spirit of the invention will be apparent to those skilled in the art. For example, as discussed above, a density-based float can be used with many hydrogen-rich liquid or gaseous fuels. Many different types of fuel-release systems are possible. The float can be in contact with different mechanical or electrical control valves or triggers used to actively or passively control the feeding of fuel into the anode reservoir. Fuel release can also be set to occur at any predetermined fuel concentration. Various different shapes, colors, sizes, orientations and positions of the window, float, and fuel scale may be used. For instance, the fuel scale may lie beside a rhomboidal window, or wrap around an oblong window. Alternatively, the anode reservoir or float chamber may be made entirely from a transparent material and lack a fuel scale.

The foregoing description, for purposes of explanation used specific nomenclature to provide a thorough understanding of the invention. However, it will be apparent to one skilled in the art that the specific details are not required in order to practice the invention. In other instances, well-known portions of fuel cells are shown as diagrams in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed. Obviously many modifications and variations are possible in view of the above teachings. The embodiments are shown and described in order to best enable others skilled in the art to best utilize the invention and various embodiments with various modifications as are suited to the particular use contemplated. It is intended that the scope of the invention be defined by the following claims and their equivalents:

What is claimed is:

1. A fuel cell comprising:
    an anode where fuel is oxidized;
    a cathode where oxygen is reduced;
    an anode reservoir that contains a fuel solution and the anode; and
    a float responsive to fuel solution density immersed in a volume of fuel solution that serves as a fuel-concentration indicator.

2. The fuel cell of claim 1 wherein the fuel solution is a solution of methanol in water.

3. The fuel cell of claim 1 wherein the volume of the fuel solution is contained within a float chamber in fluid contact with the anode reservoir and separated from the anode reservoir by a semi-permeable filter membrane.

4. The fuel cell of claim 1 wherein the volume of the fuel solution is contained within a float chamber in fluid contact with the anode reservoir and separated from the anode reservoir by a fuel channel.

5. The fuel cell of claim 4 further including a semi-permeable membrane between the fuel solution in the anode reservoir and the fuel solution in the float chamber.

6. The fuel cell of claim 1 further comprising a fuel scale aligned with a transparent window on an exterior surface of the fuel cell in fluid communication with the volume of fuel solution.

7. The fuel cell of claim 1 wherein the float contains a fuel indicator bar.

8. The fuel cell of claim 1 wherein the float controls release of the fuel solution.

9. The fuel cell of claim 8 wherein the float completes an electrical circuit controlling the release of the fuel solution.

10. A method for determining the concentration of fuel in a fuel solution in a fuel cell having an anode reservoir containing a fuel solution, the method comprising:
    adding a float to the fuel solution within the anode reservoir of the fuel cell where fuel is oxidized, the fuel cell additionally including a cathode where oxygen is reduced; and
    determining the concentration of fuel in the fuel solution by comparing the position of the float to numeric values contained on a fuel scale.

11. The method of claim 10 wherein determination of the concentration of fuel in the fuel solution is determined by viewing the position of the float through a transparent window.

12. The method of claim 10 wherein determination of the concentration of fuel in the fuel solution is determined by viewing the position of the float through a transparent window of a float chamber, the float chamber in fluid contact with the anode reservoir and separated from the anode reservoir by a semi-permeable membrane.

13. The method of claim 10 wherein determination of the concentration of fuel in the fuel solution is determined by viewing the position of the float through a transparent window of a float chamber, the float chamber in fluid contact with the anode reservoir and separated from the anode reservoir by a fuel channel.

14. The method of claim 13 further including a semi-permeable membrane between the fuel solution in the anode reservoir and fuel solution in the float chamber.

15. The method of claim 10 wherein the fuel solution is a solution of methanol fuel in water.

* * * * *